(12) United States Patent
Wey

(10) Patent No.: US 6,363,285 B1
(45) Date of Patent: Mar. 26, 2002

(54) THERAPEUTIC SLEEPING AID DEVICE

(76) Inventor: Albert C. Wey, 233 E. 57th St., Westmont, IL (US) 60559

( * ) Notice: Subject to any disclaimer, the term of this patent is extended or adjusted under 35 U.S.C. 154(b) by 0 days.

(21) Appl. No.: 09/488,869

(22) Filed: Jan. 21, 2000

(51) Int. Cl.$^7$ .................................................. A61F 2/00
(52) U.S. Cl. ........................................ 607/100; 607/109
(58) Field of Search ................................ 607/100, 109; 250/495.1

(56) References Cited

U.S. PATENT DOCUMENTS

| | | | | |
|---|---|---|---|---|
| 4,825,868 A | * | 5/1989 | Susa et al. .................. | 128/376 |
| 4,976,706 A | | 12/1990 | Aki et al. | |
| 5,138,133 A | | 8/1992 | Sakurada | |
| 5,451,199 A | | 9/1995 | Kim | |
| 5,814,078 A | * | 9/1998 | Zhou et al. ..................... | 607/1 |
| 5,894,067 A | | 4/1999 | Kim | |
| 6,004,344 A | * | 12/1999 | Fujii ............................ | 607/91 |
| 6,026,330 A | * | 2/2000 | Chuang ...................... | 607/100 |
| 6,108,581 A | * | 8/2000 | Jung ........................... | 607/100 |
| 6,120,531 A | * | 9/2000 | Zhou et al. ................. | 607/111 |
| 6,294,758 B1 | * | 9/2001 | Masao et al. ............... | 219/217 |

* cited by examiner

Primary Examiner—Linda C. M. Dvorak
Assistant Examiner—Jocelyn Ram
(74) Attorney, Agent, or Firm—Piper Marbury Rudnick & Wolfe; Jonathan Feuchtung, Esq.

(57) ABSTRACT

This invention describes a therapeutic sleeping aid device comprising a far infrared radiation layer on the inner surface of the device which can wrap around the user's head, thereof said far infrared radiation permeates into the skin of human being to raise subcutaneous temperature for feeling of warmth simulating the touches from human and pets, and to promote circulation and metabolism within for helping the head recover from stress and fatigue and maintain the health and function of the head while sleeping.

13 Claims, 2 Drawing Sheets

THERAPEUTIC SLEEPING AID DEVICE

BACKGROUND

1. Field of Invention

This invention relates to a therapeutic sleeping aid device comprising a far infrared radiation layer on the inner surface of the device which can wrap around the user's head, covering eyes and ears, thereof said far infrared radiation permeates into the skin of human head to raise subcutaneous temperature for keeping head warm, and to promote circulation and metabolism within for helping the head recover from stress and fatigue and maintain the health of the body while sleeping.

2. Description of Prior Art

There have been several types of devices developed for improving and maintaining health of human body using far infrared radiation. For example, one type of devices included a magnetic radiating unit on a far infrared ray generating composition plate (U.S. Pat. Nos. 5,451,199 and 5,894,067), the other devices comprised both germanium powder and ceramic powder for skin contact medical treatment (U.S. Pat. No. 4,976,706). The third devices involved a far infrared radiator with a heating means (U.S. Pat. No. 5,138,133). All of them might have recognized the potential of far infrared radiation in improving living body functions, but had either improperly used the far infrared radiation as an accessory rather than as a primary source for cure or required a heating source due to low radiation capacity of the far infrared ray emitting materials used. Nevertheless, none of the prior arts teaches the use of a farinfrared rays emitting material in the application as described herein.

It is known that far infrared radiation in a wavelength band of 3 $\mu$m to 14 $\mu$m has a strong resonance effect to substance having hydrogen bonding. According to Organic Chemistry, there exist dipole-dipole interactions between polarized molecules and hydrogen bonding is a strong form of such interactions. The electric potentials of such dipole-dipole interactions are in the range of 0.04 eV to 0.5 eV. Based on a simplified equation that governs the relationship between electric potential (eV) and the photon energy E associated with a wavelength $\lambda(\mu m)$: $\lambda(\mu m)=1.2398$ $(eV\mu m)/E(eV)$, such dipole-dipole interactions will resonate with the electromagnetic waves having wavelengths between 2.5 $\mu$m to 30 $\mu$m, which fall in the far infrared radiation zone.

For example, Water molecule consists of two hydrogen (H) atoms and one oxygen (O) atom. The angle between the two oxygen-hydrogen chemical bonding (O—H) in water molecule is 104° so that the water molecules are polarized in nature. It means that the hydrogen atoms and oxygen atoms in water molecules are charged and tend to create a static hydrogen bonding between each other. As a result, the charged water molecules gather and form large clusters. The hydrogen bonding between water molecules has an electric potential about 0.35 eV and can be resonantly broken with a radiation at about 3.54 $\mu$m wavelength into individual molecules or smaller molecule clusters with better mobility. In addition, a 6.27 $\mu$m far infrared radiation can activate the water molecules by transferring photon energy of the radiation into symmetrical rotation of atoms in water molecules.

Therefore, water is a good absorbent of far-infrared radiation at the wavelengths 3.54 $\mu$m and 6.27 $\mu$m. The photon energies of far-infrared radiation are absorbed by clustered water molecules and used to break apart the clusters and charge up the molecules. The forced-apart water molecules, or smaller clusters, remain polarized (or called "energized") after absorbing the photons. Meanwhile, the energized water molecules tend to stabilize by regaining cluster formation with others. When it happens, photons with the same characteristics, namely the same wavelengths and photon energies, are released based on the Principle of Conservation of Momentum. The newly released photons can be recycled to break apart another clusters until they fully dissipate as heat or escape from the system. This makes water a great medium for "transporting" photon energy of far infrared radiation.

The photon energies absorbed by the skin can permeate 4 to 5 cm into human body and energize the water molecules and cells within. The "energized" water molecules and cells in human body are active and mobile so that it can promote metabolism and blood circulation. Consequently, far-infrared radiation is "propagated" in the human body by riding on water molecules that are circulating in the body systems, as water constructs over 70% of human body while the highly polymerized human body is made of protein, cells, nucleic acid, enzymes, and so on.

Numerous clinical studies have manifested various effects of far infrared radiation on human bodies such as rise in subcutaneous temperature, enhancement of blood circulation and metabolism, mitigation of sensitive nerves, and so on. Studies also demonstrated that exposure to far infrared radiation could activate the strained molecules in stressed muscles and help recover from fatigue.

It is further understood that cancer-causing effects are cumulative at the cell level. Improved metabolism and blood circulation based on energized water molecules can prevent cancer-causing factors from accumulating in human body. For example, far infrared radiation from the device may affect the cell molecules of human brain and cause some change therein to correct the adverse effects caused by EMF (electromagnetic field) radiation from the uses of cell phone in the day time and prevent, minimize, or slow down the cumulative cancer-causing effects. There is some evidence that while EMF may not directly cause cancer, it may sometimes combine with chemical agents to promote its growth or inhibit the work of the body's immune system. The device of the present invention can correct the damage done by the EMF from cell phones or other appliance and equipment.

The far infrared ray emitting body is typically composed of oxides selected from the group consisting alumina, silica, alumina hydrate, silica hydrate, zirconia, lithium oxide, magnesium oxide, calcium oxide, titanium oxide, or a mixture of said oxides.

The present inventor has undertaken extensive studies to select a far infrared rays generating composition that possesses a strong radiation capacity in the desirable band of wavelengths, namely 3 to 14 $\mu$m. Accordingly, the inventor found that the far infrared ray generating composition fabricated by the method involving inorganic powders having particle sizes smaller than 3,000 angstroms provided a larger radiation effect that could be attributed to larger specific radiation surface areas of the particles. The inventor further found that only those far infrared rays emitting body comprising mixtures of compounds having ultrafine inorganic powders with particle sizes smaller than 1,000 angstroms, preferably below 200 angstroms, would emit considerable radiation that could effectively activate the water at a rather significant level.

Therefore, this invention relates to a therapeutic sleeping aid device comprising a far infrared rays emitting material made of ultrafine powders. The device can not only reduce noise and eliminate unwanted light with eyes and ears covered, but also provide a therapeutic means for improving blood circulation and metabolism in the brain, preventing sinus congestion, minimizing the possibility of hearing loss, recovering form stress and fatigue, stimulating skin and hair care action, reducing cumulative cancer-causing effects, and so on. Furthermore, the rise in subcutaneous temperature resulted from the far infrared radiation of the device can create a feeling of warmth similar to that from the touches by human being or pets that much differs from other heating means and can help rest or sleep better.

OBJECTS AND ADVANTAGES

Accordingly, one object of this invention is to provide a sleeping aid device that helps the user rest or sleep better.

Another object of the present invention is to provide a simple, easy-to-use, and effective therapeutic device that enhances the function and health of the head.

Another object of the present invention is to provide a simple, easy-to-use, and yet effective therapeutic device that helps the head recover from stress and fatigue.

Another object of the present invention is to provide a simple, easy-to-use, and yet effective therapeutic device that helps maintaining the health and function of ears, nose and throat.

Another object of the present invention is to provide a simple, easy-to-use, and yet effective therapeutic device that may prevent the brain from accumulating cancer-causing effects.

Another object of the present invention is to provide a simple, easy-to-use, and yet effective therapeutic device that can stimulate the skin and hair care action.

These objectives are achieved by a therapeutic sleeping aid device comprising a far infrared ray emitting material made of ultrafine powders.

Other objects, features and advantages of the present invention will hereinafter become apparent to those skilled in the art from the following description.

DRAWING FIGURES

REFERENCE NUMERALS IN DRAWINGS

11 Far infrared rays emitting material
12 Fabric sheet

SUMMARY

In accordance with the present invention a therapeutic sleeping aid device comprises a far infrared radiating material made of ultrafine powders disposed on the inner surface of a layer that can wrap around the user's head, covering eyes and ears, thereof said far infrared radiation permeates into the skin of the head to raise subcutaneous temperature for simulating the feeling of warmth from touches by human being or pets, and to promote circulation and metabolism within for helping recover from stress and fatigue and maintain the health and function of the head while sleeping.

DETAILED DESCRIPTION OF THE INVENTION

Figure 1:
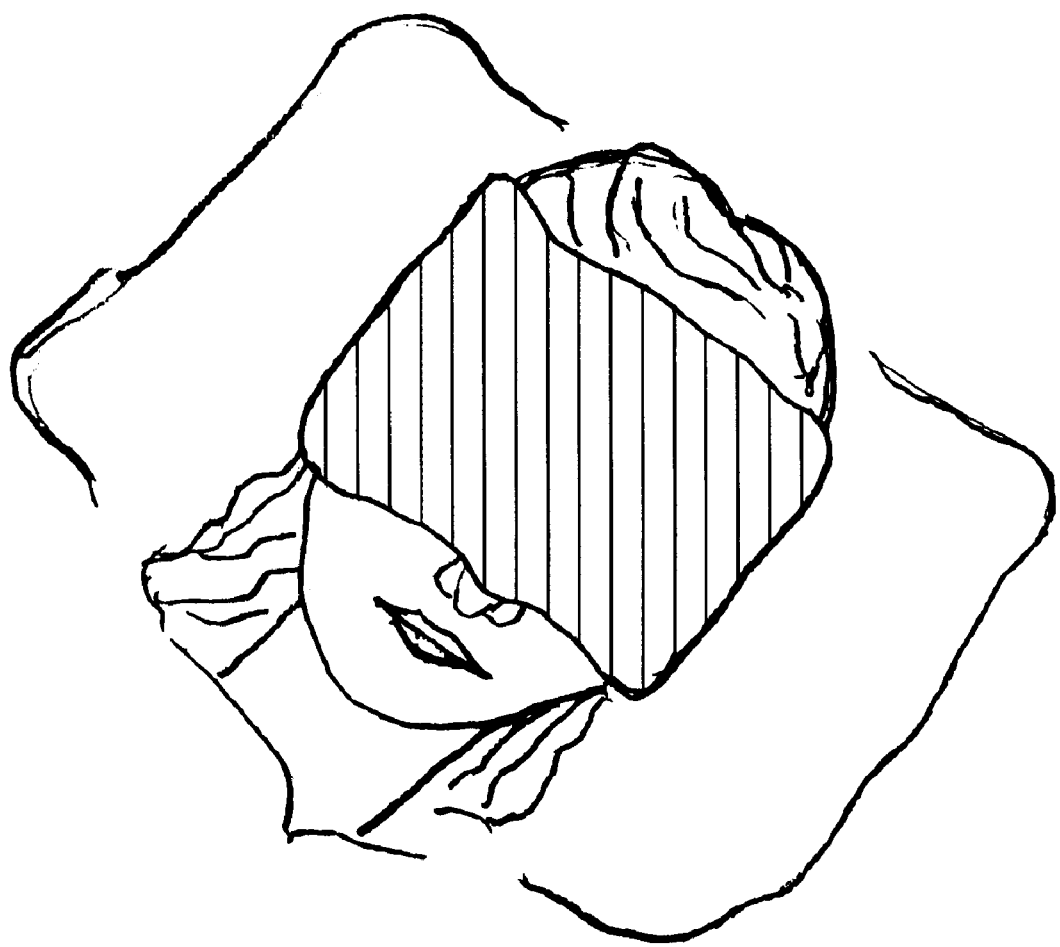
FIG. 1 shows a schematic view illustrating one embodiment of the present invention with a far infrared radiation layer on the inner surface of the device which can wrap around the user's head.
Figure 2:
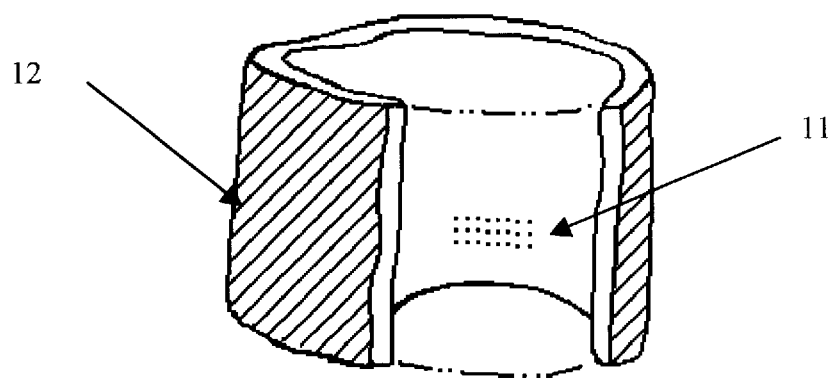
FIG. 2 shows a cutaway view of the embodiment of the present invention as shown in FIG. 1 with a far infrared rays emitting material disposed on the inner surface of the device.

FIG. 1 illustrates one embodiment of the present invention in a form of a wrap around the user's head, covering eyes and ears. It can reduce noise and eliminate unwanted light that may help the user sleep better. The device is soft, comfortable, light weight and washable, and works well in all sleeping positions, in bed or in auto or airline travel. The sheet material may be woven fabrics or the like, preferably those having gas permeability and stretchable. The device can be made in various sizes so that it may fit comfortably the heads. The device of present invention can also be made in different sizes to wrap around the neck or the waist for local treatment. FIG. 2 shows a cutaway perspective view of the embodiment as shown in FIG. 1 with the far infrared radiating material 11 disposed on a fabric sheet 12.

Figure 3:
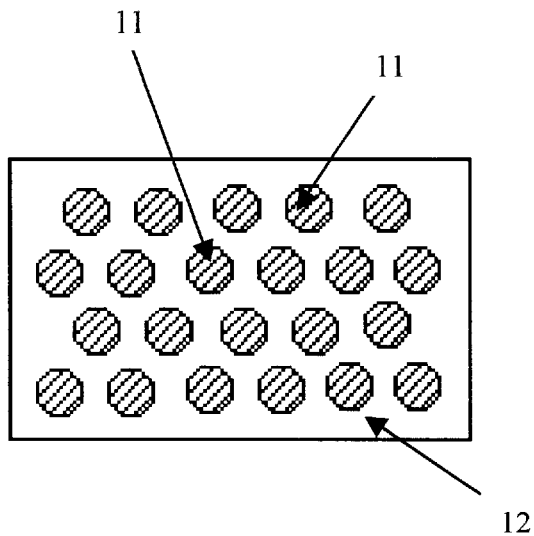
FIG. 3 is a schematic enlarged view of the inner surface of the present invention as shown in FIG. 2 with plural far infrared ray emitting elements printed on a sheet.

FIG. 3 shows a schematic plan view illustrating details of one embodiment of the present invention with plural far infrared ray emitting elements 11 printed on a sheet 12. This arrangement constitutes a basic element of far infrared ray emitting sheet material that can also be used to construct cloths, hair caps, eye masks, head bands, wrist bands, waist bands, knee support, and the like.

Figure 4:
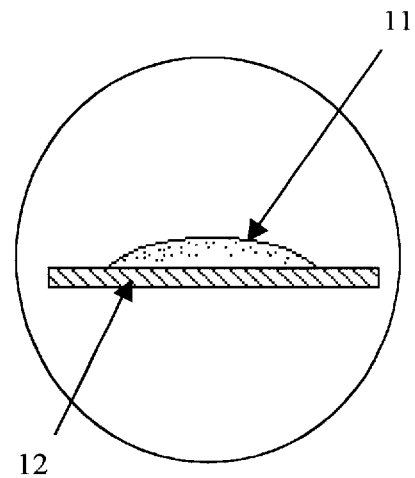
FIG. 4 is a schematic enlarged cross section of the far infrared ray emitting element on a fabric sheet as shown in FIG. 3.

The sheet material 12 may be woven fabrics, various synthetic resin films, or the like, preferably those having gas permeability. The coating of far infrared emitting material 11 on the sheet 12 can be carried out by printing the selected infrared ray emitting ceramic powders with an adhesive such as polyvinyl alcohol, silicone resin, or the like, on the surface of the sheet 12. The ceramic powders can be printed as a round spot at a diameter of 3/64 inch (1.5 mm) each and 3/64 inch (1.5 mm) apart to fill the surface area of the sheet. FIG. 4 shows a schematic enlarged cross section of the printed ceramic element 11 on the sheet 12 as shown in FIG. 3. For examples of other embodiments, the ceramic powder can also be uniformly coated on or impregnated in a pliable sheet by deposition, sputtering or other known techniques. The pliable sheet again can be woven fabrics, resin coated cloth, various synthetic resin films, or the like.

EXAMPLE

A commercially available ceramic composition that had a particle size around 200 $\mu$m and a wavelength band between 3 $\mu$m to 14 $\mu$m was chosen and used to print on a fabric sheet. The device is about 26 inches in circumference and 8 inches wide. It was reported that after three-month sleeping with the device of the present invention, the chronicle sinus congestion problem with a 46-year old patient was greatly improved.

CONCLUSION, RAMIFICATIONS, AND SCOPE

According to the present invention, a therapeutic sleeping aid device comprising a far infrared rays emitting material having a particle size smaller than 3,000 angstrom, preferably 200 angstrom or smaller, can effectively activate the cells in the human's head with its far infrared radiation. As a result, this device can help the user sleep better with a feeling of warmth and recover from stress and fatigue. The device can be used to maintain the health and function of the head or for other therapeutic purposes.

The invention has been described above. Obviously, numerous modifications and variations of the present invention are possible in light of the above teachings. Such variations are not to be regarded as a departure from the spirit and scope of the invention and all such modifications as would be obvious to one skilled in the art are intended to be included within the scope of the following claims.

I claim:

1. A therapeutic sleeping aid device, comprising:
    a far infrared ray emitting material disposed on a substrate;
    said far infrared ray emitting material including far infrared ray emitting particles having a radiation capacity in the band of wavelengths between 3 and 14 microns;
    wherein the said far infrared ray emitting material requires no additional heating source, and said infrared ray emitting particles have a size of 200 angstroms or below.

2. A device according to claim 1 wherein said far infrared ray emitting particles are selected from the group consisting of alumina, silica, alumina hydrate, silica hydrate, zirconia, lithium oxide, magnesium oxide, calcium oxide, titanium oxide, or a mixture of said oxides.

3. The device according to claim 1 wherein said substrate comprises a cloth material.

4. The device according to claim 1 wherein said substrate comprises a fabric material.

5. The device according to claim 1 wherein said substrate comprises a rubber material.

6. The device according to claim 1 wherein said substrate comprises a resin material.

7. The device according to claim 1 wherein said substrate is impregnated with said far infrared ray emitting material.

8. The device according to claim 1 wherein said substrate comprises a fabric material made of threads said threads being coated with said far infrared ray emitting material.

9. The device according to claim 1 wherein said substrate comprises a fabric material made of threads said threads, being impregnated with said far infrared ray emitting material.

10. A therapeutic sleeping aid device comprising: a substrate, and a plurality of ceramic elements, including far infrared ray emitting particles having a radiation capacity in the band of wavelengths between 3 and 14 microns, formed on said substrate, said far infrared ray emitting particles have a size of 200 angstroms or below; each ceramic element having a generally circular shape with a diameter of approximately 3/64 inch and being spaced apart from adjacent ceramic elements by approximately 3/64 inch.

11. The device according to claim 10, wherein said substrate is selected from the group comprising woven fabrics, synthetic resin films.

12. The device according to claim 10, wherein:
    said substrate is a tubular shaped piece of material having an inner surface and an exterior surface, said plurality of ceramic elements being formed on said inner surface of said substrate.

13. The device according to claim 10, wherein:
    said substrate is a hair cap having an inner surface and an exterior surface, said plurality of ceramic elements being formed on said inner surface of said substrate.

* * * * *